US00PP16814P2

(12) United States Plant Patent
Sakazaki

(10) Patent No.: US PP16,814 P2
(45) Date of Patent: Jul. 11, 2006

(54) ***ANAGALLIS* PLANT NAMED 'USANG5'**

(50) Latin Name: *Anagallis hybrida*
Varietal Denomination: USANG5

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 20 days.

(21) Appl. No.: 11/113,394

(22) Filed: Apr. 23, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Anagallis* plant named 'USANG5', characterized by its compact, low-trailing and outwardly spreading plant habit; vigorous growth habit; freely branching habit; numerous fragrant flower that are dark pink in color; and good garden performance.

1 Drawing Sheet

Botanical designation: *Anagallis hybrida.*
Cultivar denomination: 'USANG5'.

BACKGROUND OF THE INVENTION

The present Invention relates to a new and distinct cultivar of *Anagallis* plant, botanically known as *Anagallis hybrida*, and hereinafter referred to by the cultivar name USANG5.

The new *Anagallis* is a product of a planned breeding program conducted by the Inventor in Hikone Shiga, Japan. The objective of the breeding program is to creat new compact *Anagallis* plants with freely flowering habit and attractive flower coloration.

The new *Anagallis* originated from a cross-pollination made by the Inventor on May 25, 1999 of an unnamed selection of *Anagallis filiformis*, not patented, as the female, or seed parent, with an unnamed selection of *Anagallis hybrida*, not patented, as the male, or pollen parent. The new *Anagallis* was discovered and selected as a single plant from within the resulting progeny of the cross-pollination in Bonsall, Calif. on May 12, 2000.

Asexual reproduction of the new cultivar by terminal vegetative cuttings since Jul. 1, 2000 in Bonsall, Calif. has shown that the unique features of this new *Anagallis* are stable and reproduced true to type in successive generations.

SUMMARY OF THE INVENTION

Plants of the cultivar USANG5 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USANG5'. These characteristics in combination distinguish 'USANG5' as a new and distinct cultivar:

1. Compact, low trailing and outwardly spreading plant habit.
2. Vigorous growth habit.

3. Freely branching habit.
4. Numerous fragrant flowers that are dark pink in color.
5. Good garden performance.

In side-by-side comparisons conducted in Bonsall, Calif., plants of the new *Anagallis* differed from plants of the female parent selection, in the following characteristics:

1. Plants of the new *Anagallis* were more vigorous than plants of the female parent selection.
2. Plants of the new *Anagallis* had larger flowers than plants of the female parent selection.

In side-by-side comparisons conducted in Bonsall, Calif., plants of the new *Anagallis* differed from plants of the male parent selection, in the following characteristics:

1. Plants of the new *Anagallis* were more vigorous than plants of the male parent selection.
2. Plants of the new *Anagallis* had larger flowers than plants of the male parent selection.

Plants of the new *Anagallis* differ from plants of the cultivar USANG4, disclosed in U.S. Plant patent application Ser. No. 10/955,490, primarily in flower color as plants of the new *Anagallis* have darker pink-colored flowers than plants of the cultivar USANG4.

Plants of the new *Anagallis* can be compared to plants of the *Anagallis* cultivar Wildcat Orange, disclosed in U.S. Plant Pat. No. 15,136. In side-by-side comparisons conducted in Bonsall, Calif., plants of the new *Anagallis* differed from plants of the cultivar Wildcat Orange in the following characteristics:

1. Plants of the new *Anagallis* were more trailing than and not as upright as plants of the cultivar Wildcat Orange.
2. Plants of the new *Anagallis* had dark pink-colored flowers whereas plants of the cultivar Wildcat Orange had orange-colored flowers.
3. Flowers of plants of the new *Anagallis* were fragrant whereas flowers of plants of the cultivar Wildcat Orange were not fragrant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Anagallis*.

The photograph at the top of the sheet is a close-up view of typical flowers and leaves of 'USANG5'.

The photograph at the bottom of the sheet comprises a side perspective view of a typical plant of 'USANG5' grown in a container.

DETAILED BOTANICAL DESCRIPTION

The aforementioned photographs and following observations and measurements describe plants grown in Bonsall, Calif., in a polyethylene-covered greenhouse during the late spring under full sun conditions with day temperatures ranging from 18 to 35° C. and night temperatures ranging from 10 to 21° C. After planting rooted cuttings, plants were grown for about 23 weeks in one-gallon containers. Plants were pinched one time. Color references are made to The Royal Horticultural Society Colour Chart, 1995 Edition, except where general terms of ordinary dictionary significance are used.

Botanical classification: *Anagallis hybrida* cultivar USANG5.

Parentage:

*Female parent.*—Unnamed selection of *Anagallis filiformis*, not patented.

*Male parent.*—Unnamed selection of *Anagallis hybrida*, not patented.

Propagation:

*Type cutting.*—Terminal vegetative cuttings.

*Time to initiate roots, summer.*—About five days at 24° C.

*Time to initiate roots, winter.*—About seven days at 24° C.

*Time to develop roots, summer.*—About 20 days at 24° C.

*Time to develop roots, winter.*—About 25 days at 24° C.

*Root description.*—Fine, fibrous; white, close to 155D, in color.

*Rooting habit.*—Freely branching.

Plant description:

*Form/growth habit.*—Annual flowering plants; compact; initially upright, then low-trailing and outwardly spreading; uniformly mounded plant form. Freely branching habit with more than 300 lateral branches per plant. Vigorous growth habit.

*Plant height.*—About 10 cm.

*Plant diameter* (*area of spread*), *single plant.*—About 42 cm.

*Lateral branches.*—Length: About 36 cm. Diameter: About 1.5 mm. Internode length: About 1.5 cm. Texture: Smooth, glabrous. Color: 183C.

*Foliage description.—Arrangement: Opposite; simple. Length: About* 8 mm. Width: About 8 mm. Shape: Oval. Apex: Rounded. Base: Attenuate. Margin: Entire. Texture, upper and lower surfaces: Glabrous, smooth. Venation pattern: Pinnate, arcuate. Color: Developing leaves, upper and lower surfaces: 144A. Fully expanded leaves, upper surface: 137A. Fully expanded leaves, lower surface: 137B. Venation, upper surface: 137A. Venation, lower surface: 137B. Petiole: Length: About 2 mm. Diameter: About 1 mm. Texture, upper and lower surfaces: Smooth, glabrous. Color, upper and lower surfaces: 144B.

Flower description:

*Flower type and habit.*—Single star-shaped flowers; flowers face mostly upward or outward; terminally or axillary; freely flowering habit, about 36 flowers and flower buds per lateral branch.

*Natural flowering season.*—Plants flower from April through September in Bonsall, Calif.; flowering continuous during this period. Plants start flowering about six weeks after planting rooted cuttings. Flowers persistent.

*Flower longevity on the plant.*—About one week.

*Fragrance.*—Cinnamon-like.

*Flower size.*—Diameter: About 1.2 cm. Depth (height): About 8 mm.

*Flower buds.*—Length: About 6 mm. Diameter: About 2 mm. Shape: Oblong. Color: 63A.

*Petals.*—Quantity/arrangement: About five petals arranged in a single whorl. Length: About 8 mm. Width: About 4 mm. Shape: Obovate. Apex: Rounded. Base: Attenuate. Margin: Entire. Texture, upper and lower surfaces: Smooth, satiny. Color: When opening and fully opened, upper surface: 63B. When opening and fully opened, lower surface: 64D.

*Sepals.*—Arrangement/appearance: Five sepals arranged in a single whorl; star-shaped. Length: About 4 mm. Width: About 1 mm. Shape: Ligulate. Apex: Acuminate. Base: Fused. Margin: Entire. Texture, upper and lower surfaces: Smooth, glabrous. Color, upper surface: 146A. Color, lower surface: 146B.

*Peduncles.*—Length: About 3.3 cm. Width: About 1 mm. Angle: About 45° from the main stem. Strength: Strong. Texture: Smooth, glabrous. Color: 146B.

*Reproductive organs.*—Stamens: Quantity per flower: About five. Anther shape: Round. Anther length: Less than 1 mm. Anther color: 10A. Pollen amount: Scarce. Pollen color: 8A. Pistils: Quantity per flower: One. Pistil length: About 8 mm. Style length: About 5 mm. Style color: 145D. Stigma shape: Rounded. Stigma color: Close to 62B. Ovary color: 146A.

*Seed/fruit.*—Seed and/or fruit production has not been observed.

Disease/pest resistance: Plants of the new *Anagallis* have not been noted to be resistant to pathogens or pests common to *Anagallis*.

Garden performance: Plants of the new *Anagallis* have been observed to have good garden performance. Plants of the new *Anagallis* have been noted to tolerate temperatures from about 5 to 40° C. and have excellent tolerance to rain and wind.

It is claimed:

1. A new and distinct cultivar of *Anagallis* plant named 'USANG5', as illustrated and described.

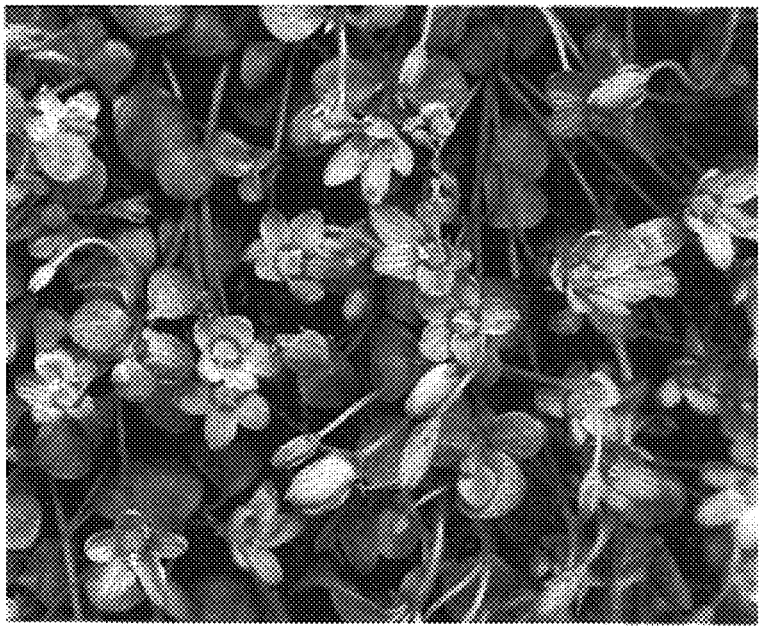
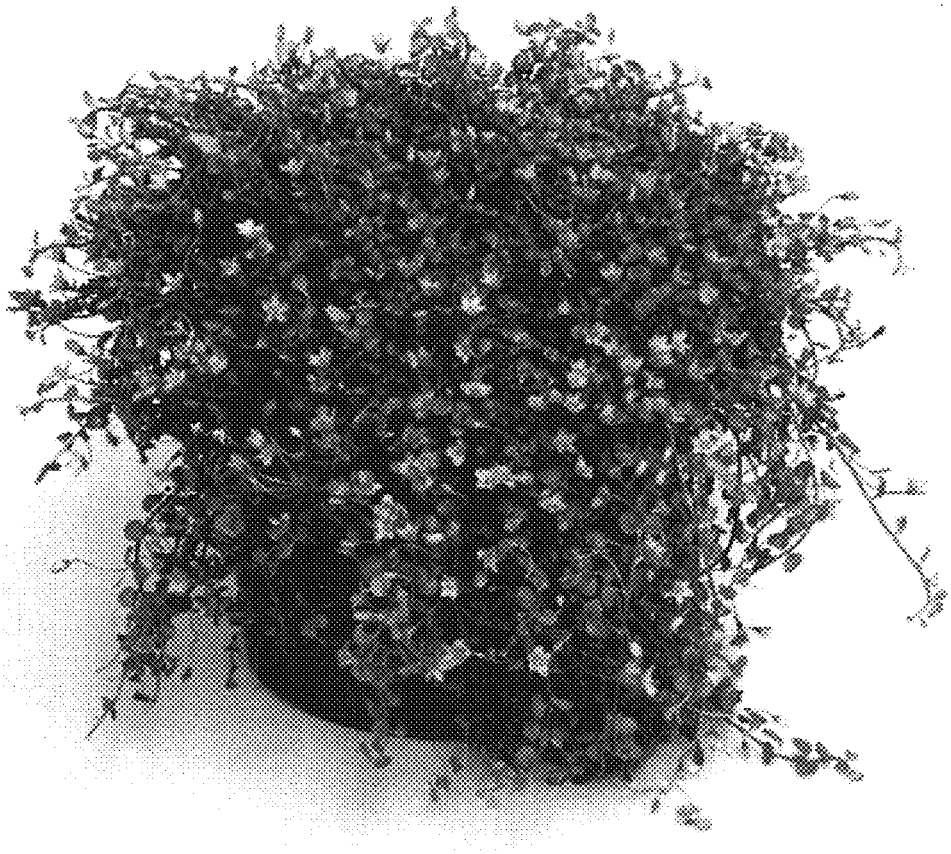

* * * * *